(12) United States Patent
Eberhard et al.

(10) Patent No.: US 6,751,285 B2
(45) Date of Patent: Jun. 15, 2004

(54) DOSE MANAGEMENT SYSTEM FOR MAMMOGRAPHIC TOMOSYNTHESIS

(75) Inventors: Jeffrey Wayne Eberhard, Albany, NY (US); Bernhard Erich Hermann Claus, Niskayuna, NY (US); Beale Opsahl-Ong, Darien, CT (US); Ralph Allen Hewes, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/990,114

(22) Filed: Nov. 21, 2001

(65) Prior Publication Data

US 2003/0095624 A1 May 22, 2003

(51) Int. Cl.[7] .................................................. A61B 6/04
(52) U.S. Cl. ....................................................... 378/37
(58) Field of Search ........................................... 378/37

(56) References Cited

U.S. PATENT DOCUMENTS

| | | | | | |
|---|---|---|---|---|---|
| 4,875,478 | A | * | 10/1989 | Chen | 378/37 |
| 5,335,257 | A | * | 8/1994 | Stunberg | 378/37 |
| 5,526,394 | A | * | 6/1996 | Siczek et al. | 378/37 |
| 5,627,869 | A | * | 5/1997 | Andrew et al. | 378/37 |

OTHER PUBLICATIONS

"Force" Conversion Table, http://conversion.com/maribi.com/conversion/force.htm.*

* cited by examiner

*Primary Examiner*—Craig E. Church
(74) *Attorney, Agent, or Firm*—Robert B. Reeser, III; Armstrong Teasdale LLP

(57) ABSTRACT

A method for acquiring a plurality of images of an object of interest using a tomosynthesis imaging system. The method includes determining a thickness of an object of interest, and adjusting at least one parameter of an image acquisition process based on the determined thickness.

30 Claims, 3 Drawing Sheets

| Number of Angles | Target (Anode) | Filter | Radiation source Voltage | mAs |
|---|---|---|---|---|
| 8 | Rhodium | Rhodium | 28 | 100 |
| 8 | Rhodium | Rhodium | 30 | 100 |
| 8 | Rhodium | Rhodium | 32 | 140 |
| 8 | Molybdenum | Molybdenum | 24 | 100 |
| 8 | Molybdenum | Molybdenum | 26 | 125 |
| 8 | Molybdenum | Molybdenum | 28 | 110 |
| 8 | Molybdenum | Rhodium | 28 | 110 |
| 11 | Rhodium | Rhodium | 28 | 110 |
| 11 | Rhodium | Rhodium | 30 | 110 |
| 11 | Rhodium | Rhodium | 32 | 110 |
| 11 | Molybdenum | Molybdenum | 24 | 125 |
| 11 | Molybdenum | Molybdenum | 26 | 140 |
| 11 | Molybdenum | Molybdenum | 28 | 140 |
| 11 | Molybdenum | Rhodium | 28 | 140 |

FIG. 3

DOSE MANAGEMENT SYSTEM FOR MAMMOGRAPHIC TOMOSYNTHESIS

STATEMENT REGARDING FEDERALLY SPONSORED RESEARCH & DEVELOPMENT

The government may have rights in this invention pursuant to Grant DAMD17-98-1-8109 issued from the US Army Medical Research and Materiel Command.

BACKGROUND OF THE INVENTION

This invention relates generally to tomosynthesis and more particularly to a method and apparatus for acquiring a plurality of images using a tomosynthesis imaging system using a reduced compression force.

In at least some known imaging systems, a radiation source projects a cone-shaped beam which passes through the object being imaged, such as a patient and impinges upon a rectangular array of radiation detectors. In some known tomosynthesis systems, the radiation source rotates with a gantry around a pivot point, and views of the object are acquired for different projection angles. As used herein "view" refers to a single projection image or, more particularly, "view" refers to a single projection radiograph which forms a projection image. Also, as used herein, a single reconstructed (cross-sectional) image, representative of the structures within the imaged object at a fixed height above the detector, is referred to as a "slice". And a collection (or plurality) of views is referred to as a "projection dataset." A collection of (or a plurality of) slices for all heights is referred to as a "three-dimensional dataset representative of the image object."

One known method of reconstructing a three-dimensional dataset representative of the imaged object is known in the art as simple backprojection, or shift-and-add. Simple backprojection backprojects each view across the imaged volume, and averages the backprojected views. A "slice" of the reconstructed dataset includes the average of the backprojected images for some considered height above the detector. Each slice is representative of the structures of the imaged object at the considered height, and the collection of these slices for different heights, constitutes a three-dimensional dataset representative of the imaged object.

In some known imaging systems, a compression force is applied to a breast to improve image quality by reducing a thickness of the breast thereby spreading the breast tissue over a larger area. The reduction in the breast thickness, and spreading the breast over a larger area, facilitate interpretation of the projection radiographs, because the amount of "overlying tissue" for structures within the imaged breast is minimized in the projection radiograph. Reduction of the breast thickness by compression is also important in managing a patient radiation dosage. In general, the thicker the compressed breast, the more x-ray attenuation. Therefore, a higher dosage is applied to a thicker breast to keep an x-ray signal level at the detector essentially constant. This is particularly important in a film/screen system, where the film is not appropriately "blackened" if the radiation dosage is either too high or too low. Some known patients may experience discomfort due to the compression force applied to the breast and may not schedule any future examinations, thereby possibly increasing the patient's risk that a serious medical condition may not be detected in a timely fashion.

BRIEF DESCRIPTION OF THE INVENTION

In one embodiment, a method for acquiring a plurality of images of an object of interest using a tomosynthesis imaging system is provided. The method includes determining a thickness of an object of interest, and adjusting at least one parameter of an image acquisition process based on the determined thickness.

In another embodiment, a method for operating a tomosynthesis imaging system is provided. The method includes providing an object of interest and generating a mammographic compressed thickness of the object. The method also includes adjusting the mammographic compressed thickness by adding one-half centimeter to the mammographic compressed thickness when the mammographic compressed thickness is less than four and one-half centimeters thick and adding one centimeter to the mammographic compressed thickness when the mammographic compressed thickness is at least four and one-half centimeters thick, and using the adjusted mammographic compressed thickness to perform a tomosynthesis scan.

In a further embodiment, a tomosynthesis imaging system for acquiring a plurality of images of an object of interest is provided. The tomosynthesis imaging system includes a detector array, at least one radiation source, a compression force indicator, a compressed breast thickness indicator, and a computer coupled to the detector array and the radiation source. The computer is configured to determine a thickness of an object of interest and adjust at least one parameter of an image acquisition process based on the determined thickness.

In a still further embodiment, a computer readable medium encoded with a program executable by a computer for controlling an imaging system is provided. The imaging system includes a radiation source and a digital detector. The program is configured to instruct the computer to determine a thickness of an object of interest and adjust at least one parameter of an image acquisition process based on the determined thickness.

BRIEF DESCRIPTION OF THE DRAWINGS

FIG. 3 is a table depicting techniques used for projection dataset acquisition for a tomosynthesis system

DETAILED DESCRIPTION OF THE INVENTION

Figure 1:
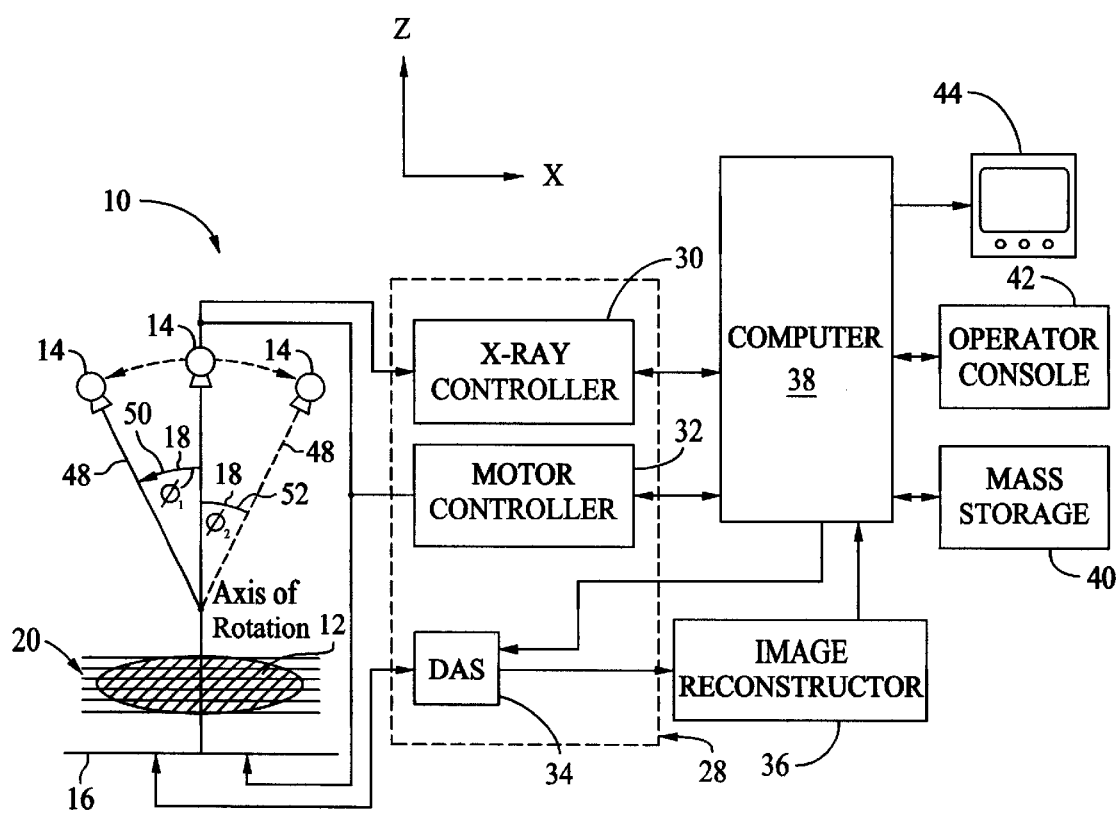
FIG. 1 is a pictorial view of an imaging system.

Referring to FIG. 1 and in an exemplary embodiment, a digital imaging system 10 generates a three-dimensional dataset representative of an imaged object 12, such as a patient's breast 12 in mammographic tomosynthesis. System 10 includes at least one radiation source 14, such as an x-ray source 14, and at least one detector array 16 for collecting views from a plurality of projection angles 18. Specifically and in one embodiment, system 10 includes a radiation source 14 which projects a cone-shaped beam of x-rays which pass through object 12 and impinge on detector array 16. The views obtained at each angle 18 can be used to reconstruct a plurality of slices, i.e., images representative of structures located in planes 20 parallel to detector 16. Detector array 16 is fabricated in a panel configuration having a plurality of pixels (not shown) arranged in rows and columns so that a view is generated for an entire object of interest such as breast 12. In one embodiment, each pixel of detector array 16 includes a photosensor, such as a photodiode, that is coupled via a switching transistor to two separate address lines, a scan line and a data line. The radiation incident on a scintillator material and the pixel photosensors measure, by way of change in the charge across the diode, the amount of light generated by x-ray interaction with the scintillator. As a result, each pixel of detector array 16 produces an electronic signal that represents the intensity, after attenuation by object 12, of an x-ray beam impinging on the pixel of detector array 16. In one embodiment, detector array 16 is approximately 20 cm by 20 cm and is configured to produce views for an entire object of interest, e.g., breast 12. Alternatively, detector array 16 is variably sized depending on the intended use.

In one embodiment, the reconstructed three-dimensional dataset is not arranged in slices corresponding to planes that are parallel to detector 16, but in a more general fashion. In another embodiment, the reconstructed dataset consists only of a single two-dimensional image, or one-dimensional function. In yet another embodiment, detector 16 is a shape other than planar, or other than rectangular.

In one embodiment, radiation source 14 and detector array 16 are moveable relative to the object 12 and each other. More specifically, radiation source 14 and detector array 16 can be positioned so that the projection angle 18 of the imaged volume is altered. Radiation source 14 and detector array 16 can be positioned such that projection angle 18 may be any acute or oblique projection angle. In another embodiment, only radiation source 14 is moveable relative to object 12 and detector array 16.

The operation of radiation source 14 is governed by a control mechanism 28 of imaging system 10. Control mechanism 28 includes a radiation controller 30 that provides power and timing signals to radiation source 14 and a motor controller 32 that controls the respective positioning speed and position of radiation source 14 and detector array 16. A data acquisition system (DAS) 34 in control mechanism 28 samples digital data from detector 16 for subsequent processing. An image reconstructor 36 receives sampled and digitized projection dataset from DAS 34 and performs image reconstruction. The reconstructed three-dimensional dataset, representative of imaged object 12, is applied as an input to a computer 38 which stores the three-dimensional dataset in a mass storage device 40. Radiation controller 30 and motor controller 32 are programmed to perform functions described herein, and, as used herein, the term controller refers to computers, processors, microcontrollers, microcomputers, programmable logic controllers, application specific integrated circuits, and other programmable circuits.

Computer 38 also receives commands and scanning parameters from an operator via console 42 that has an input device. A display 44, such as a cathode ray tube and a liquid crystal display (LCD) allows the operator to observe the reconstructed three-dimensional dataset and other data from computer 38. The operator supplied commands and parameters are used by computer 38 to provide control signals and information to DAS 34, motor controller 32, and radiation controller 30. In one embodiment, control mechanism 28 receives thickness information of compressed breast 12, and automatically adjusts motion and radiation control parameters accordingly, as described herein. In one embodiment the thickness information is received from an operator, via console 42, in another embodiment, the information is received directly from a breast thickness indicator (not shown).

In use, a patient is positioned such that the object of interest 12 is within the field of view of system 10, i.e., breast 12 is compressed and positioned within the imaged volume extending between radiation source 14 and detector array 16. Views of breast 12 are then acquired from at least two projection angles 18 to generate a projection dataset of the volume of interest. The plurality of views represent the tomosynthesis projection dataset. The collected projection dataset is then utilized to generate a three-dimensional dataset, i.e., a plurality of slices for scanned breast 12, representative of the three-dimensional radiographic representation of imaged breast 12.

Figure 2:
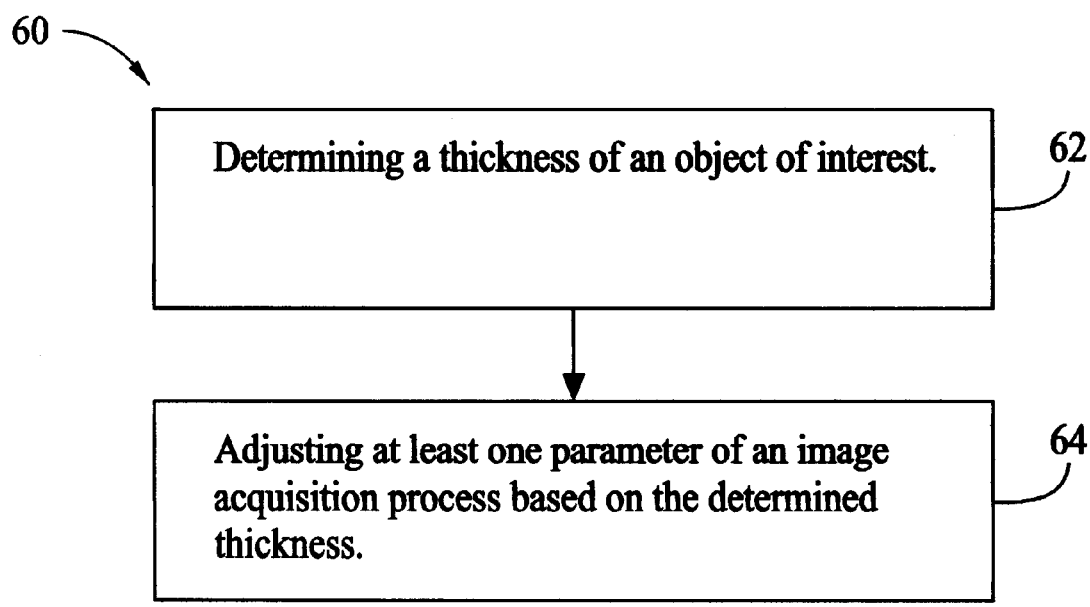
FIG. 2 is a flow diagram of a method including acquiring views of an object.

FIG. 2 is a flow diagram of a method 60 of acquiring a plurality of images of an object of interest using a tomosynthesis imaging system 10. Method 60 includes determining 62 a thickness of an object of interest and adjusting 64 at least one parameter of an image acquisition process based on the determined thickness. Method 60 also includes acquiring a first view using the adjusted parameter, adjusting at least one parameter based on the acquired view and acquiring a second view based on the parameter adjusted after acquiring the first view.

In one embodiment, imaging system 10 includes a compressed breast thickness indicator 63 (shown in FIG. 1), and a compression force indicator 65 (shown in FIG. 1). In one embodiment, compressed breast thickness indicator 63 and compression force indicator 65 are digital indicators. Alternatively, compressed breast thickness indicator 63 and compression force indicator 65 are analog indicators. In another embodiment, a compressed breast thickness and a compression force, as determined by the respective indicator, are displayed on imaging system display 44 (shown in FIG. 1). In another embodiment, the compressed thickness and the compression force are available as inputs to control mechanism 28.

Determining 62 a thickness of object of interest 12 includes applying a compression force to object of interest 12. In use, object of interest 12, such as a breast 12, is positioned using a digital imaging system 10 (shown in FIG. 1), such as tomosynthesis imaging system 10. Imaging system 10 then applies a compression force of less than 22 decaNewtons. A thickness is then determined after a required compression force, which is less than the corresponding compression force used in standard mammography, has been applied to breast 12. In one embodiment, the compression force and the compressed breast thickness are determined by imaging system 10. Alternatively, the compression force may be adjusted or pre-selected by an operator, via operator console 42.

In one embodiment, adjusting 64 at least one parameter of an image acquisition process based on the determined thickness includes adjusting at least one of an acquisition geometry parameter, a radiation control parameter, a data acquisition parameter, and a reconstruction parameter. In one embodiment, adjusting an acquisition geometry parameter includes, but is not limited to, adjusting a projection angle 18 (shown in FIG. 1). In use, breast 12 is positioned in imaging system 10 (shown in FIG. 1), a thickness is determined as described herein, and at least one parameter of an image acquisition process is adjusted based on the determined thickness. Radiation source 14 (shown in FIG. 1) is then enabled such that a radiation beam is emitted at first projection angle 50 (shown in FIG. 1), a first view is acquired using detector array 16 (shown in FIG. 1). Projection angle 18 (shown in FIG. 1) of system 10 is then altered by modifying the position of radiation source 14 such that central axis 48 (shown in FIG. 1) of the radiation beam is altered to a second projection angle 52 (shown in FIG. 1) and position of detector array 16 is altered so that breast 12 remains within the field of view of system 10. Radiation source 14 is again enabled and a second view is acquired for second projection angle 52. The same procedure is then repeated for any number of subsequent projection angles 18.

In one embodiment, adjusting 64 at least one parameter of an image acquisition process based on the determined thickness also includes adjusting a radiation control parameter, such as, but not limited to, adjusting at least one of a source anode, a radiation source filter, a radiation source voltage, a radiation source current, and a radiation exposure time.

In one embodiment, adjusting 64 at least one parameter based on the determined thickness includes imaging breast 12 with a reduced compression which results in a greater thickness of breast 12. In one embodiment, using radiation source 14 spectrum, a higher dose can be delivered to avoid a reduction of image quality, i.e. signal to noise ratio in the image. Alternatively, the radiation dosage can be reduced by increasing the energy of the x-rays used in the image acquisition process as explained below.

For example, by increasing the tube voltage, or by removing a molybdenum anode and a molybdenum filter (Mo/Mo) and installing a molybdenum anode and a rhodium filter (Mo/Rh), or installing a rhodium anode and a rhodium filter (Rh/Rh), the x-rays become more penetrating and the signal delivered to detector 16 is increased. A reduced image contrast due to increased energy x-rays is compensated for by an increased detector signal to noise ratio. Therefore, using a harder x-ray spectrum for a less compressed breast 12 facilitates an acceptable x-ray penetration of breast 12 and a sufficient signal to noise ratio in the detected signal at a reasonable dosage. Dose management is therefore achieved by using higher energy x-rays to decrease the x-ray attenuation through breast 12, thereby generating images with a lower patient dosage. In one embodiment, radiation source 14 includes a single anode and a single filter. In an alternative embodiment, radiation source 14 includes a plurality of anodes and a plurality of filters, wherein the anodes and the filters can be changed while acquiring views of object 12 from at least two projection angles. Further, advanced x-ray tube technology, using additional or alternative anode and filter materials, may be used to facilitate hardening of the x-ray spectrum, thereby increasing the x-ray penetration and the image quality, while keeping patient dosage at a reasonable level.

In one embodiment, adjusting 64 at least one parameter of an image acquisition process based on the determined thickness also includes adjusting a radiation control parameter. In one embodiment, the radiation source voltage, current, or the exposure time can be modified in each view to appropriately manage the dose. In another embodiment, the number of exposures, and the angular positions of the radiation source for these exposures, can be adjusted. For example, imaging system 10 includes a radiation controller 30 configured to provide approximately the same total dose in the multiple tomosynthesis views as required in a standard mammogram. In one embodiment, processing of the views by computer 38 or data acquisition system 34 can generate images indicative of the tissue composition. Further, this processing can also include a suitable management of image noise.

FIG. 3 is a table depicting typical techniques used for exposure in tomosynthesis system 10, using an eight or eleven angle configuration. The techniques shown in FIG. 3 result in a patient dose comparable to the dose in a single mammographic view. In one embodiment, and referring to FIG. 3, the patient dose corresponding to the values indicated in FIG. 3 can be doubled for a reasonable patient dosage management. Additionally, further patient dose increases in diagnostic applications can be used where the single tomosynthesis acquisition and evaluation may replace as many as 10 exposures during a clinical examination.

In one embodiment, adjusting 64 at least one parameter of an image acquisition process based on the determined thickness also includes adjusting a data acquisition parameter, such as, but not limited to, adjusting detector 16 gain.

In one embodiment, the projection dataset is acquired without the use of an anti-scatter grid. Imaging without using an anti-scatter grid facilitates a reduction in patient radiation dosage because the absence of an anti-scatter grid allows a reduced dosage to be applied to breast 12 to achieve the same signal to noise ratio in the single views. In addition, appropriate scatter correction algorithms may be applied to the views in the projection dataset, which will allow for further noise management.

In one embodiment, the electronic gain of detector 16 can be increased to facilitate managing noise in low dose acquisitions. In one embodiment the gain is equal to a ratio between approximately 1.45 and approximately 1.65. In another embodiment, gain is equal to a ratio of approximately 1.55. In a further embodiment, the gain is equal to a ratio between approximately 1.35 and approximately 1.75. Alternatively, gain can be selectively chosen by the operator depending on the compressed breast thickness. In a further embodiment, the gain is approximately inversely proportional to the dose per view, and is equal to a ratio less than, or equal to 4.0.

Further, low electronic noise in detector 16 facilitates an improvement in image quality. In one embodiment, the electronic gain of detector 16 is adjusted for tomosynthesis projection dataset acquisition. The electronic gain can be increased to facilitate managing noise in low dose acquisitions. In one embodiment the gain can be adjusted automatically by control mechanism 28 as a function of the compressed thickness and exposure technique.

In one embodiment, adjusting 64 at least one parameter of an image acquisition process based on the determined thickness includes adjusting a reconstruction parameter, such as, but not limited to adjusting a thickness of a reconstructed volume and adjusting the quantity of reconstructed slices.

Adjusting a thickness of a reconstructed volume and adjusting the quantity of reconstructed slices includes pre-processing the projection data, backprojecting the projection data across an imaged volume, and reconstructing an image of the object of interest such that a view intensity is distributed over the determined thickness only. In an alternative embodiment, other known reconstruction algorithms are used to reconstruct a three-dimensional representation of the imaged object, which does not extend in height beyond the compressed thickness.

In one embodiment, pre-processing at least one view and reconstructing at least one image of the object of interest using the pre-processed view includes using the compressed thickness information. For example, compressed breast thickness information can be used to improve the image quality of the reconstructed tomosynthesis images by forcing the reconstructed breast tissue corresponding to an intensity in any view to be distributed over the known compressed thickness of the breast only, instead of over a larger or smaller volume if the compressed thickness were not known.

In one embodiment, a specific quantity of slices of breast 12, such as but not limited to fifty slices, are reconstructed without regard to the thickness of breast 12, i.e. the same quantity of slices are generated for any breast 12 thickness. A reduction in breast compression results in a thicker image volume and therefore facilitates improved image quality because the information in the z-direction, i.e. a height above detector array 16 will be extended over a larger volume.

In one embodiment, tomosynthesis system 10 acquires data over a limited range of angles, due to the constraint to keep breast 12 and detector 16 stationary. For example, imaging system 10 can have an angular range which is limited to 54 degrees, resulting in a reconstructed 3-dimensional image of breast 12 with a z-directional spatial resolution significantly less than in the x-y plane. Typical values are 0.1 mm in the x-y plane and approximately 1 mm in the z-direction. In another embodiment, imaging system 10 can have an angular range, such as, but not limited to 60 degrees and 90 degrees.

Adjusting 64 at least one parameter of an image acquisition process based on the determined thickness also includes using various combinations of higher electronic gain in the detector for tomosynthesis mode, higher energy x-rays for better penetration, and an adjusted x-ray current and/or exposure time in each view. After at least one parameter has been modified as a function of the compressed breast thickness and the second projection angle, a second image is acquired. In one embodiment, the projection angles and other parameters are modified for each individual view acquired during the scanning process. Alternatively, a plurality of views may be acquired prior to modifying at least one parameter, and prior to completing the scanning process. In one embodiment, the parameters or a subset of parameters for each view are selected by the operator, as a function of the determined thickness. Further, all remaining parameters or a subset of the remaining parameters for each view are determined by computer 38 as a function of the compressed thickness. In an exemplary embodiment, a method for operating a tomosynthesis imaging system 10 includes providing an object of interest 12, generating a mammographic compressed thickness of object 12, and adjusting the mammographic compressed thickness by adding one-half centimeter to the mammographic compressed thickness when the mammographic compressed thickness is less than four and one-half centimeters thick and adding one centimeter to the mammographic compressed thickness when the mammographic compressed thickness is at least four and one-half centimeters thick. The method also includes using the adjusted mammographic compressed thickness to perform a tomosynthesis scan.

For example, a breast 12 is provided. A technician skilled in the operation of a mammographic system generates a compressed breast thickness of breast 12. Generating a compressed breast thickness of breast 12 includes estimating the compression force to be applied to breast 12 using a standard mammography system (not shown) to obtain a desired mammographic compressed breast thickness. The technician then applies a reduced compression force, i.e. a compression force that is less than a compression force used in mammography. In one embodiment, the technician applies a reduced compression force such that the mammographic compressed breast thickness is increased by approximately 0.5 cm for breasts with a compressed thickness between approximately 2–4 cm, is increased by approximately 0.75 cm for breasts between approximately 4–6 cm, is increased by approximately 1.0 cm for breasts between approximately 6–8 cm, and is increased by approximately 1.25 cm for breasts greater than 8 cm compressed thickness. Breast 12 is then placed in tomosynthesis imaging system 10 and a compression force is applied until the adjusted compressed breast thickness is reached. Images can then be acquired in accordance with tomosynthesis scanning methods described herein.

In use, an increase in compressed breast of 0.5 cm for breasts with a compressed thickness between 2–4 cm, 0.75 cm for breasts between 4–6 cm, 1.0 cm for breasts between 6–8 cm, and 1.25 cm for breasts of more than 8 cm compressed thickness facilitates a reduction in patient discomfort. Although some compression force is required to reduce patient motion during the tomosynthesis examination process, an increase in compressed thickness as compared to standard mammography as described herein is enough to facilitate a more comfortable examination and still provide image quality sufficient to significantly enhance the performance of tomosynthesis compared to conventional mammography.

While the invention has been described in terms of various specific embodiments, those skilled in the art will recognize that the invention can be practiced with modification within the spirit and scope of the claims.

What is claimed is:

1. A method for acquiring a plurality of images of a breast using a tomosynthesis imaging system, said method comprising:
    estimating a compression force to be applied to a breast wherein the force would be substantially equal to a force necessary to acquire an image if using a mammographic imaging system;
    applying a compression force greater than 0 decaNewtons and less than approximately 22 decaNewtons to the breast using the tomosynthesis imaging system, wherein the compression force applied is less than the estimated compression force;
    determining a thickness of the compressed breast;
    adjusting at least one parameter of an image acquisition process based on the determined thickness;
    scanning the breast to generate a three-dimensional dataset; and
    generating at least one three-dimensional image of the compressed breast using the three-dimensional dataset.

2. A method in accordance with claim 1 further comprising:
    acquiring a first view using the adjusted parameter;
    adjusting at least one parameter based on the acquired view; and
    acquiring a second view based on the parameter adjusted after acquiring the first view.

3. A method in accordance with claim 1 wherein adjusting at least one parameter of an image acquisition process comprises adjusting at least one of an acquisition geometry parameter, a radiation control parameter, a reconstruction parameter, wherein adjusting the reconstruction parameter comprises adjusting at least one of a thickness of a reconstructed volume, and a quantity of reconstructed slices, and a data acquisition parameter wherein adjusting the data acquisition parameter comprises adjusting a detector gain.

4. A method in accordance with claim 1 wherein adjusting at least one parameter of an image acquisition process comprises adjusting at least one of an acquisition geometry parameter, a radiation control parameter, a reconstruction parameter, and a data acquisition parameter wherein adjusting the data acquisition parameter comprises adjusting a detector gain.

5. A method in accordance with claim 1 wherein adjusting at least one parameter of an image acquisition process comprises adjusting at least one of an acquisition geometry parameter, a radiation control parameter, and a reconstruction parameter, wherein the acquisition geometry parameter comprises a geometry parameter to acquire a first view at a first angle and a second view at a second angle.

6. A method in accordance with claim 1 wherein adjusting at least one parameter of an image acquisition process comprises adjusting at least one of an acquisition geometry parameter, a radiation control parameter, and a reconstruction parameter, wherein the radiation control parameter comprises at least one of a radiation source anode, a radiation source filter, a radiation source voltage, a radiation source current, and a radiation exposure time.

7. A method for acquiring a plurality of images of a breast using a tomosynthesis imaging system, said method comprising:
    estimating a compression force to be applied to a breast wherein the force would be substantially equal to a force necessary to acquire an image if using a mammographic imaging system;
    applying a compression force greater than 0 decaNewtons and less than approximately 22 decaNewtons to the breast using the tomosynthesis imaging system, wherein the compression force applied is less than the estimated compression force;
    determining a thickness of the breast based on the compression force applied using the tomosynthesis imaging system;
    adjusting at least one of a geometry parameter to acquire a first view at a first angle and a second view at a second angle, a radiation source anode, a radiation source filter, a radiation source voltage, a radiation source current, a radiation exposure time, a thickness of a reconstructed volume, a detector gain, and a quantity of reconstructed slices, based on the determined thickness;
    scanning the breast to generate a three-dimensional dataset; and
    generating at least one three-dimensional image of the compressed breast using the three-dimensional dataset.

8. A method for operating a tomosynthesis imaging system, said method comprising:
    providing an object of interest;
    estimating a first compression force to apply to the object of interest using a known mammography system, wherein an operator applies the first compression force to the object of interest until a patient experiences discomfort;
    applying a second compression force, less than the first compression force, to the object of interest;
    adjusting the second compression force such that a mammographic compressed breast thickness is increased by 0.5 cm for breasts having a compressed breast thickness of 2–4 cm, is increased by 0.75 cm for breasts having a compressed breast thickness between 4–6 cm, is increased by 1.0 cm for breasts having a compressed breast thickness between 6–8 cm, and is increased by 1.25 cm for breasts having a compressed breast thickness greater than 8 cm; and
    using the adjusted mammographic compressed thickness to perform a tomosynthesis scan.

9. A method in accordance with claim 8 further comprising adjusting at least one parameter of an image acquisition process.

10. A method in accordance with claim 9 wherein adjusting at least one parameter of an image acquisition process comprises adjusting at least one of an acquisition geometry parameter, a radiation control parameter, and a reconstruction parameter, wherein said reconstruction parameter comprises at least one of a thickness of a reconstructed volume, and a quantity of reconstructed slices.

11. A method in accordance with claim 9 wherein adjusting at least one parameter of an image acquisition process comprises adjusting at least one of an acquisition geometry parameter, a radiation control parameter, and a reconstruction parameter, wherein said acquisition geometry parameter comprises a geometry parameter to acquire a first view at a first angle and a second view at a second angle.

12. A method in accordance with claim 9 wherein adjusting at least one parameter of an image acquisition process comprises adjusting at least one of an acquisition geometry parameter, a radiation control parameter, and a reconstruction parameter, wherein said radiation control parameter comprises at least one of a radiation source anode, a radiation source filter, a radiation source voltage, a radiation source current, and a radiation exposure time.

13. A method in accordance with claim 8 further comprising:
    acquiring a first view of the object of interest;
    adjusting at least one parameter based on the acquired view; and
    acquiring a second view based on the parameter adjusted after acquiring the first view.

14. A method in accordance with claim 13 wherein adjusting at least one parameter of an image acquisition process comprises adjusting at least one of an acquisition geometry parameter, a radiation control parameter, a reconstruction parameter, and a data acquisition parameter wherein adjusting the data acquisition parameter comprises adjusting a detector gain.

15. A method in accordance with claim 8 further comprising applying a compression force less than approximately 22 decaNewtons to the object of interest.

16. A tomosynthesis imaging system for acquiring a plurality of images of a breast, said tomosynthesis imaging system comprising;
    a detector array comprising a plurality of pixels arranged in rows and columns;
    at least one radiation source;
    a compression force indicator;
    a compressed breast thickness indicator; and
    a computer coupled to said detector array and said radiation source and configured to:
        compress the breast, using the tomosynthesis imaging system, until a patient experiences discomfort;
        reduce the compression force applied to the breast such that a mammographic compressed breast thickness is increased by at least approximately 0.5 cm;
        determine a thickness of the breast based on the reduced compression force;
        adjust at least one parameter of an image acquisition process based on the determined thickness of the breast;
        scan the breast such that a plurality of two-dimensional images of the breast are generated; and
        generate at least one three-dimensional image of the breast using the plurality of two-dimensional images of the breast.

17. A tomosynthesis imaging system in accordance with claim 16 wherein to adjust at least one parameter of an image acquisition process, said computer further configured to adjust at least one of an acquisition geometry parameter, a radiation control parameter, and a reconstruction parameter wherein said reconstruction parameter comprises at least one of a thickness of a reconstructed volume, and a quantity of reconstructed slices.

18. A tomosynthesis imaging system in accordance with claim 16 wherein to adjust at least one parameter of an image acquisition process, said computer further configured to adjust at least one of an acquisition geometry parameter, a radiation control parameter, and a reconstruction parameter wherein said radiation control parameter comprises at least one of a radiation source anode, a radiation source filter, a radiation source voltage, a radiation source current, and a radiation exposure time.

19. A tomosynthesis imaging system in accordance with claim 16 wherein said computer further configured to:
   acquire a first view using the adjusted parameter;
   adjust at least one parameter based on the acquired view; and
   acquire a second view based on the parameter adjusted after acquiring the first view.

20. A tomosynthesis imaging system in accordance with claim 16 wherein said computer further configured to apply a compression force less than approximately 22 decaNewtons to the breast.

21. A tomosynthesis imaging system in accordance with claim 16 wherein to adjust at least one parameter of an image acquisition process, said computer further configured to adjust at least one of an acquisition geometry parameter, a radiation control parameter, a reconstruction parameter, and a data acquisition parameter wherein adjusting the data acquisition parameter comprises adjusting a detector gain.

22. A tomosynthesis imaging system in accordance with claim 16 wherein to adjust at least one parameter of an image acquisition process, said computer further configured to adjust at least one of an acquisition geometry parameter, a radiation control parameter, and a reconstruction parameter wherein said acquisition geometry parameter comprises a geometry parameter to acquire a first view at a first angle and a second view at a second angle.

23. A tomosynthesis imaging system for acquiring a plurality of images of a breast, said tomosynthesis imaging system comprising;
   a detector array comprising a plurality of pixels arranged in rows and columns;
   at least one radiation source;
   a compression force indicator;
   a compressed breast thickness indicator; and
   a computer coupled to said detector array and said radiation source and configured to:
     compress the breast, using the tomosynthesis imaging system, until a patient experiences discomfort;
     reduce the compression force applied to the breast such that a mammographic compressed breast thickness is increased by at least approximately 0.5 cm;
     determine a thickness of the breast based on the reduced compression force;
     adjust at least one of a geometry parameter to acquire a first view at a first angle and a second view at a second angle, a radiation source anode, a radiation source filter, a radiation source voltage, a radiation source current, a radiation exposure time, a thickness of a reconstructed volume, and a quantity of reconstructed slices based on the determined thickness of the breast;
     scan the breast such that a plurality of two-dimensional images of the breast are generated; and
     generate at least one three-dimensional image of the breast using the plurality of two-dimensional images.

24. A computer readable medium encoded with a program executable by a computer for controlling an imaging system, the imaging system including a radiation source and a digital detector, said program configured to instruct the computer to:
   estimate a compression force to be applied to a breast wherein the force would be substantially equal to a force necessary to acquire an image if using a mammographic imaging system;
   apply a compression force greater than 0 decaNewtons and less than approximately 22 decaNewtons to an object of interest wherein the compression force applied is less than the estimated compression force;
   determine a thickness of the object of interest;
   adjust at least one parameter of an image acquisition process based on the determined thickness; scan the breast such that a plurality of two-dimensional images of the breast are generated; and
   generate at least one three-dimensional image of the breast using the plurality of two-dimensional images.

25. A computer readable medium in accordance with claim 24 wherein said program further configured to instruct the computer:
   acquire a first view using the adjusted parameter;
   adjust at least one parameter based on acquired view; and
   acquire a second view based on the parameter adjusted after acquiring the first view.

26. A computer readable medium in accordance with claim 24 wherein to adjust at least one parameter of an image acquisition process, said computer further configured to adjust at least one of an acquisition geometry parameter, a radiation control parameter, a reconstruction parameter, and a data acquisition parameter wherein adjusting the data acquisition parameter comprises adjusting a detector gain.

27. A computer readable medium in accordance with claim 24 wherein to adjust at least one parameter of an image acquisition process, said computer further configured to adjust at least one of an acquisition geometry parameter, a radiation control parameter, and a reconstruction parameter wherein said acquisition geometry parameter comprises a geometry parameter to acquire a first view at a first angle and a second view at a second angle.

28. A computer readable medium in accordance with claim 24 wherein to adjust at least one parameter of an image acquisition process, said computer further configured to adjust at least one of an acquisition geometry parameter, a radiation control parameter, and a reconstruction parameter wherein said radiation control parameter comprises at least one of a radiation source anode, a radiation source filter, a radiation source voltage, a radiation source current, and a radiation exposure time.

29. A computer readable medium in accordance with claim 24 wherein to adjust at least one parameter of an image acquisition process, said computer further configured to adjust at least one of an acquisition geometry parameter, a radiation control parameter, and a reconstruction parameter wherein said reconstruction parameter comprises at least one of a thickness of a reconstructed volume, and a quantity of reconstructed slices.

30. A computer readable medium encoded with a program executable by a computer for calibration of a tomosynthesis imaging system, the imaging system including a radiation source and a digital detector, said program configured to instruct the computer to:

estimate a compression force to be applied to a breast wherein the force would be substantially equal to a force necessary to acquire an image if using a mammographic imaging system;

apply a compression force greater than 0 decaNewtons and less than approximately 22 decaNewtons to the breast using the tomosynthesis imaging system, wherein the compression force applied is less than the estimated compression force;

determine a thickness of the breast based on the compression force applied using the tomosynthesis imaging system; and adjust at least one of a geometry parameter to acquire a first view at a first angle and a second view at a second angle, a radiation source anode, a radiation source filter, a radiation source voltage, a radiation source current, a radiation exposure time, a thickness of a reconstructed volume, and a quantity of reconstructed slices based on the determined thickness of the breast scan the breast to generate a three-dimensional dataset; and generate at least one three-dimensional image of the compressed breast using the three-dimensional dataset.

* * * * *